(12) United States Patent
Tanimoto et al.

(10) Patent No.: US 6,960,477 B2
(45) Date of Patent: Nov. 1, 2005

(54) CLOSED HEAT-DECOMPOSING APPLIANCE, PRETREATMENT METHOD OF SAMPLE USING IT, ANALYTICAL METHOD AND DEVICE THEREFOR

(75) Inventors: Noriyuki Tanimoto, Hiroshima-ken (JP); Yoshimitsu Tada, Tokuyama (JP); Hideo Morinaka, Tokuyama (JP); Tadashi Okada, Shinnanyo (JP)

(73) Assignee: Tosoh Corporation, Yamaguchi-ken (JP)

( * ) Notice: Subject to any disclaimer, the term of this patent is extended or adjusted under 35 U.S.C. 154(b) by 0 days.

(21) Appl. No.: 09/774,641

(22) Filed: Feb. 1, 2001

(65) Prior Publication Data

US 2001/0016356 A1 Aug. 23, 2001

Related U.S. Application Data

(62) Division of application No. 09/206,161, filed on Dec. 7, 1998, now abandoned.

(30) Foreign Application Priority Data

Dec. 5, 1997 (JP) .............................................. 9-336132

(51) Int. Cl.$^7$ .............................. G01N 1/10; B01L 3/00
(52) U.S. Cl. ........................ 436/175; 422/68.1; 422/78; 422/80; 422/99; 436/155; 436/160; 436/174
(58) Field of Search .......................... 422/68.1, 78, 80, 422/83, 88, 99, 102, 103; 436/160, 155, 174–175

(56) References Cited

U.S. PATENT DOCUMENTS

| | | | | |
|---|---|---|---|---|
| 3,296,435 A | * | 1/1967 | Teal et al. ................... | 436/146 |
| 3,716,334 A | * | 2/1973 | Pont ............................ | 205/780 |
| 3,734,127 A | * | 5/1973 | Williams et al. ............ | 137/583 |
| 3,776,695 A | * | 12/1973 | Peterson ...................... | 436/59 |
| 4,025,309 A | * | 5/1977 | Hach ............................ | 422/78 |
| 4,054,414 A | * | 10/1977 | Grob et al. .................. | 436/115 |
| 4,160,802 A | * | 7/1979 | White et al. .............. | 422/82.09 |
| 4,234,315 A | * | 11/1980 | Scott ............................ | 436/115 |
| 4,401,763 A | * | 8/1983 | Itoh ............................. | 436/115 |
| 4,485,071 A | * | 11/1984 | Larter .......................... | 422/78 |
| 4,616,938 A | | 10/1986 | Bonnard ....................... | 374/38 |
| 5,064,617 A | * | 11/1991 | O'Brien et al. ............. | 356/312 |
| 5,395,586 A | * | 3/1995 | Hemzy et al. .............. | 414/176 |
| 5,429,846 A | * | 7/1995 | Sugimoto et al. .......... | 428/34.4 |
| 5,429,946 A | * | 7/1995 | Baccanti ...................... | 436/103 |
| 5,866,072 A | * | 2/1999 | Bowe et al. ................. | 422/64 |
| 6,458,328 B1 | * | 10/2002 | Wreyford ..................... | 422/78 |

FOREIGN PATENT DOCUMENTS

| | | | |
|---|---|---|---|
| JP | | 46-1248 | 9/1971 |
| JP | | 6-3441 | 12/1994 |
| JP | | 8-26200 | 11/1996 |
| JP | | 9274030 A | * 10/1997 |

* cited by examiner

*Primary Examiner*—Jill Warden
(74) *Attorney, Agent, or Firm*—Jacobson Holman PLLC

(57) ABSTRACT

Disclosed are a closed heat-decomposing appliance comprising a heating section with one side closed and other side having common ground portion, screw portion or O-ring-mounted portion and a closed introducing section that allows to connect to this heating section and common ground portion, screw portion or O-ring via O-ring-mounted portion and has cock or valve as a mechanism for closing and introducing the absorbing liquid to absorb the testing components from outside after heat-decomposition, or has packing or septum to introduce the absorbing liquid with needle pipe as well, and a pretreatment method of sample using this appliance. The purpose is to provide a closed heat-decomposing appliance for the pretreatment on accurate quantitative determination or detection of the testing components in sample, which requires no combustion assistant, which is not obstructed by ash present in sample absorbing the testing components, which requires no complicated and dangerous procedures, which can be used repeatedly, and which allows to inject the absorbing liquid after heat-decomposition, and a pretreatment method using it.

13 Claims, 6 Drawing Sheets

US 6,960,477 B2

CLOSED HEAT-DECOMPOSING APPLIANCE, PRETREATMENT METHOD OF SAMPLE USING IT, ANALYTICAL METHOD AND DEVICE THEREFOR

This is a division of application Ser. No. 09/206,161, filed Dec. 7, 1998 now abandoned.

BACKGROUND OF THE INVENTION

The present invention relates to a closed heat-decomposing appliance for the pretreatment on analyzing the components in a sample which may sometimes contain organics and a pretreatment method using it. In more detail, it relates to a closed heat-decomposing appliance for heat-decomposing organics and then absorbing the analyzed components into absorbing liquid on analyzing quantitatively or detecting the components in a sample which may sometimes contain organics by quantitative determination or detection, and a pretreatment method for heat-decomposing the sample and absorbing the testing components in sample using it. Moreover, it relates to a device automating the decomposition of sample, absorption of analyzed components and analysis, using the closed heat-decomposing appliance.

So far, for the analysis of components like halogen and sulfur in organics, usually pretreatment procedures of decomposing the organics under heat or combustion and absorbing the analyzed components has been done and then quantitative analysis has been performed by ion chromatography, titration, colorimetry, ion selective electrode method or the like. As the methods of this pretreatment, closed flask combustion method, combustion-tube method, sealed tube dry combustion method, hot-flask combustion method and vertical closed tube method are known.

Thereamong, the oxygen-flask method is described, for example, in "Yuki biryo teiryo bunseki" (Organic Quantitative Microanalysis) edited by "Yuki biryo teiryo kenkyuu kondankai" (Conversazione for Studying Organic Microanalysis), p. 383 (1969), Nankodo. Procedures are as follows: Namely, absorbing liquid is poured in a reaction vessel like Erlenmeyer flask, oxygen is filled up in the vessel, around several tens mg of sample is weighed, wrapped in filter paper being a combustion assistant, held between platinum meshes and fired, then this is inserted swiftly into the reaction vessel, which is turned upside down while securely pressing down the stopper and reaction vessel. During combustion of sample, the absorbing liquid blocks off the opening between flask and stopper, and, after combustion, the reaction vessel is shaken well to absorb the testing components into absorbing liquid. This oxygen-flask method requires no particular appliance to be prepared except reaction vessel, but has problems that the microanalysis is impossible due to contamination from filter paper that wraps the sample, a reaction vessel with size of an order of several hundreds ml must be used to secure the quantity of oxygen required for burning filter paper, thus requiring broad area for the space of experiment, that the skill is needed for the procedures such as firing the sample and burning it in the reaction vessel, and so on.

The combustion tube-burning method is described in detail, for example, by Honma et al in Analytical Chemistry, vol. 35, p. 536 (1986). Procedures are as follows: Namely, sample is inserted into a tube made of quartz or the like installed in a high-temperature furnace while flowing oxygen stream, and burned completely through catalyst, thereby gasfying the testing components to absorb into absorbing liquid. This combustion tube-burning method is suitable for the automation due to simple procedures, but, when ash content such as alkali metal is contained in the sample, it has drawbacks that the analyzed components transfer incompletely to absorbing liquid due to capture by ash content to make it difficult to perform accurate analysis, and the like.

The sealed tube-burning method is described in detail, for example, by Hozumi et al in Analytical Chemistry, vol. 38, p. 259 (1989). Procedures are as follows: Namely, overall sealed tube with the sample and oxygen sealed therein is inserted into a high-temperature furnace to heat and, after allowed to stand for cooling, the sealed portion is dropped into a vessel accommodated with absorbing liquid to break. Since the absorbing liquid enters forcibly into sealed tube due to negative pressure inside the sealed tube, it is allowed to stand as it is to absorb the analyzed components into absorbing liquid. This sealed tube-burning method has advantages that there is little contamination due to no combustion assistant used and that the quantity of sample is sufficient with trace amount under 1 mg, but it has drawbacks that troublesome operation of sealing tube is required for every sample, that the used sealed tubes should be disposed, thus being uneconomical, that heat-resistant materials such as quartz glass cannot be used virtually due to difficult operation of sealing tube, thereby heating of sealed tube becomes up to 600° C. at most, resulting in impossibility to decompose fire-resistant sample, and the like.

For the hot flask method, three ways of decomposing and absorbing methods are known and these are referred conveniently to as "horizontal-rotating system", "vertical system" and "horizontal system".

Thereamong, the "horizontal-rotating method" is described in detail, for example, by W. J. Kirsten in Microchem. J., vol. 7, p. 34 (1963). Procedures are as follows; Namely, a one-sidedly closed quartz tube with a bulge provided near entrance, in which bulge an absorbing liquid is accommodated, is inserted horizontally into a furnace of 850° C. until this side of the absorbing liquid portion to heat, and oxygen is filled up. Then, a quartz bar having the sample thereon is inserted swiftly to close the quartz tube therewith. The closed portion is allowed to rotate downward by 90° together with furnace to decompose the sample. After heated for several minutes, the quartz tube closed with quartz bar is taken out from furnace, cooled, and shaked to absorb the analyzed components into absorbing liquid. This "horizontal-rotating method" has advantages that there is little contamination due to no combustion assistant used and that the quantity of sample is sufficient with trace amount under several mg, but has drawbacks (1) that, since the inner pressure increases due to evaporation of absorbing liquid which is closed in vessel, possibility to cause the leakage is high, (2) that it is dangerous to swiftly insert the quartz bar having organics thereon into the tube heated to 850° C., (3) that, since the tube of which absorbing liquid portion exists nearby furnace is kept heated at 850° C., there is a possibility for absorbing liquid to evaporate up, and (4) that, since the overall furnace is rotated by 90°, a robust material is required.

The "vertical system" is described in detail, for example, by W. J. Kirsten in Microchem. J., vol. 7, p. 34 (1963). Procedures are as follows: Namely, oxygen is filled up in a one-sidedly closed quartz tube installed vertically in a furnace of 850° C. A vessel with the absorbing liquid accommodated therein is inserted swiftly from bottom of quartz tube together with quartz bar having the sample thereon and closed to decompose the sample. Through the diffusion of combustion gas, the testing components are absorbed into absorbing liquid. This "vertical system" has advantage that there is little contamination due to no combustion assistant used and that the quantity of sample is sufficient with trace amount under several mg, but has drawbacks (1) that the memory effect is observed due to residual ash and, since the quartz bar having the sample thereon is not washed with absorbing liquid, it is unsuitable for a sample containing ash, (2) that, since the inner pressure increases due to evaporation of absorbing liquid which is closed leaving accommodate as it is, possibility to cause the leakage is high, and (3) that it is dangerous to swiftly insert the vessel, which accommodates absorbing liquid therein, into the tube heated to 850° C. together with the quartz bar having the sample thereon.

The "horizontal system" is described in detail, for example, by M. E. Fernandopulles et al in Microchem. J., vol. 11, p. 41 (1966). Namely, comparing with "horizontal-rotating system", modifications are made to raise the temperature of furnace from 1000 to 1050° C. and not to rotate by 90° after closure. This "horizontal system" has advantages that there is little contamination due to no combustion assistant used and that the quantity of sample is sufficient with trace amount under several mg, but has drawbacks (1) that, since the inner pressure increases due to evaporation of absorbing liquid which is closed leaving accommodated as it is, possibility to cause the leakage is high, (2) that it is dangerous to swiftly insert the quartz bar having organics thereon into the tube heated over 1000° C. and (3) that, since the vessel with absorbing liquid portion existing nearby furnace is kept over 1000° C., there is a possibility for absorbing liquid to evaporate up.

As described, the hot flask method has advantages of little contamination due to no combustion assistant used and the quantity of sample sufficient with trace amount under several mg, but has drawbacks due to the existence of absorbing liquid in the vessel on decomposing the sample, and the like.

The vertical type closed tube method is described in detail, for example, by Kikushige Ono, in Summary of Presentations, p. 9 (1996) at Joint Symposium of 63rd Conversazione for Studying Organic Microanalysis of The Japan Society for Analytical Chemistry and 7th Sectional Meeting for Measuring Mass and Force of the Instrumentation and Automatic Control Society. Procedures are as follows: Namely, sample wrapped in combustion assistant is dropped from the top of vertical closed combustion tube heated in furnace, oxygen is blown in from oxygen blowoff port at the upper portion of tube to burn while rotating the sample in the circumferential direction, and combustion gas is passed additionally through filler portion to burn completely. Then, the absorbing liquid is injected from a mechanism for injecting absorbing liquid and all portions including combustion section is washed to absorb the testing components. This vertical type closed tube method has an advantage of less obstruction by ash content etc. because of washing combustion section, too, but has drawbacks that there is a possibility for the washing of filler placed in combustion tube to become insufficient, which remains a memory to contaminate next sample, that the mechanism of washing is complicated, and that the microanalysis is impossible due to contamination from combustion assistant.

As described above, conventional decomposition methods aiming at the analysis of components in organics has their merits and demerits. Moreover, as for the devices automated each method, there have been problems for each method.

The purpose of the invention is, replacing the conventional appliances used for the pretreatment on analyzing the components of halogen and sulfur in a sample which may sometimes contain organics, methods using them and devices automated them, to provide a closed heat-decomposing appliance (hereinafter referred to as "inventive appliance") for the pretreatment on accurate quantitative analysis or detection of the analyzed components in sample, which requires no combustion assistant, which is not obstructed by ash content present in sample absorbing the analyzed components, which requires no complicated and dangerous procedures, which can be used repeatedly, and which allows to inject the absorbing liquid after heat-decomposition, a pretreatment method (hereinafter referred to as "inventive pretreatment method") using it, for heat-decomposing the sample which may sometimes contain organics and further dissolving the testing components in sample, a pretreatment device (hereinafter referred to as "inventive pretreatment device") automates it, further a method (hereinafter referred to as "inventive analytical method") for analyzing the testing components after pretreatment, and a device (hereinafter referred to as "inventive analytical device") therefor.

SUMMARY OF THE INVENTION

As a result of diligent investigations to solve the problems aforementioned, the inventors have developed a closed heat-decomposing appliance being an appliance for horizontally or slantly injecting heating section into an electric furnace to heat, decomposing the inner organic s in the presence of oxygen gas, taking out from the electric furnace and cooling, then introducing the absorbing liquid to absorb the analyzed components, comprising a heating section made of quartz, hard glass or ceramic with one side closed and other side having ground joint, screwjoint or O-ring-mounted joint and a closed introducing section that allows to connect to this heating section and ground glass joint screw joint or O-ring-mounted joint via O-ring-mounted portion and has cock or valve as a mechanism for closing and introducing the absorbing liquid to absorb the testing components from outside after heat-decomposition, or has packing or septum to introduce the absorbing liquid with needle pipe as well. Further, they have found following knowledges by implementing a method for heat-decomposing a sample which may sometimes contain organics using this appliance and for absorbing the testing components in sample, leading to the completion of the invention.

1) There is little contamination due to no combustion assistant used.

2) Since the heat-decomposing section of sample is also washed, there is no obstruction due to ash present in the sample absorbing the testing components.

3) There are no complicated dangerous procedures such as firing of sample and combustion in flask, sealing tube operation, insertion of sample into heating area and rotation of heat-decomposing tube together with furnace.

4) Since the absorbing liquid is injected after heating, there are no anxieties of increased inner pressure due to evaporation on heating and evaporation of absorbing liquid.

5) The inventive appliance can be used repeatedly.

6) The quantity of halogen and sulfure in sample can be quantitatively analyzed accurately.

Furthermore, they have developed a device automating the pretreatments of heat-decomposition of sample and dissolution of testing components produced into absorbing liquid, using the inventive appliance, and a device automating also the analysis of testing components, leading to the completion of the invention.

Besides, in this specification, "inventive method" is sometimes quoted in the case of describing both "inventive pretreatment method" and "inventive analytical method", and "inventive device" is sometimes quoted in the case of describing both "inventive pretreatment device" and "inventive analytical device".

DETAILED DESCRIPTION OF THE INVENTION

Figure 1:
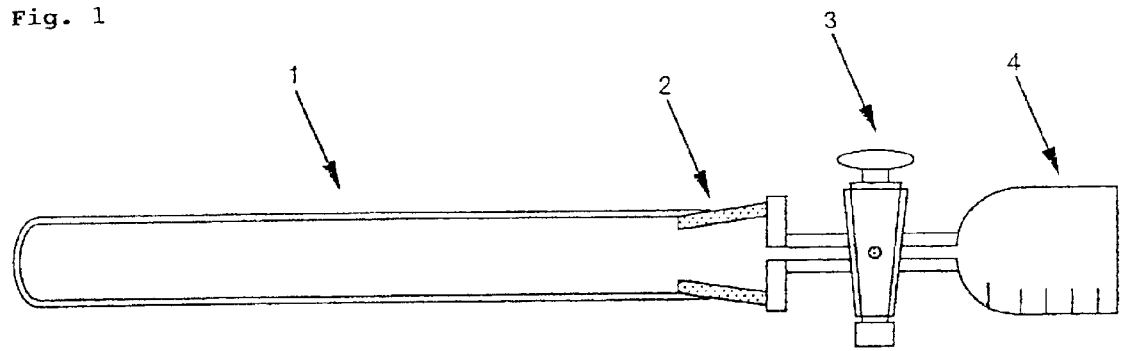
FIG. 1 is a schematic diagram of cross section of the inventive appliance in the axial direction.

In following, the invention will be explained in detail.

The material for heating section of the inventive appliance is not particularly restricted, provided 1) that no testing components are retained onto that material through adsorption etc. so that overall amounts of them transfer to the absorbing liquid on next absorbing treatment, 2) that the material is hard to be corroded with oxygen to be filled up in the inventive appliance and corrosive gases such as hydrogen halide, halogen gas and sulfur dioxide capable of generating from decomposed sample, 3) that the material can withstand enough to heating during treatment, and further 4) that the material can be molded as the heating section of the inventive appliance, and, for example, quartz, hard glass, ceramics such as alumina, zirconia and titania, and the like can be used depending on the purpose. Thereamong, since the sample inside the appliance can be observed and also heat resistance is excellent, quartz is used preferably.

The thickness of heating section of the inventive appliance may be such that taking in and out of sample are easy and the heat from furnace that is the heating device to heat the inventive appliance is transferred sufficiently, thereby causing no unevenness of temperature in heating section and incomplete combustion of sample, and usually thickness of around not less than 5 mm and not more than 30 mm is used.

The length of heating section of the inventive appliance is not particularly restricted, if the sample can burn completely. However, in the case of thicker heating section of the inventive appliance, the sample in appliance is heat-decomposed and the generating gas sometimes comes out of furnace without burning completely, thus the length is preferable to be not less than 10 cm to avoid this.

The quantity of oxygen gas to be supplied to heating section of the inventive appliance is preferably not less than 2.5 times, more preferably not less than 3 times the quantity of oxygen (hereinafter referred to as "theoretical quantity of oxygen") required for the complete combustion of sample. In case of this range, sample burns completely, resulting in improved analytical accuracy of sample. Besides, the theoretical quantity of oxygen is a quantity of oxygen required to oxidize the constituting elements in sample with oxygen, and can be calculated theoretically from the chemical composition of sample.

The shape of heating section of the inventive appliance is not particularly restricted and, for example, cylindrical tube, conical tube with heating section bulged, prismatic tube, etc. can be mentioned.

The heating device with heating means to heat the inventive appliance and to heat-decompose the sample is not particularly restricted, if it has a heating mechanism capable of completely burning the sample and can install the inventive appliance, but one provided a furnace shaped so that it can evenly heat the inside of appliance by coming close to the inventive appliance is preferable, and further a heating device provided with electric furnace easy to control the heating temperature is used preferably. While depending also on the shape of heating section of the inventive appliance, for example, if the shape is circular, a heating device provided with circular furnace is used preferably. In this way, use of the heating device provided with furnace shaped complementarily with the shape of heating section of the inventive appliance as described above makes it possible to heat evenly, which is preferable.

The material of an area contacting with decomposition gas of the sample in the closed introducing section of the inventive appliance is not particularly restricted, provided 1) that no testing components are retained onto that material through adsorption etc. so that overall amounts of them are transferred to the absorbing liquid on next absorbing treatment, 2) that the material is hard to be corroded with corrosive gases such as hydrogen halide, halogen molecule gas and sulfur dioxide capable of generating from decomposed sample, 3) that the material can withstand enough to the heat of radiation from furnace during treatment, and further 4) that the material can be molded as the closed introducing section of the inventive appliance, and, for example, quartz, hard glass, platinum, ceramics such as alumina, zirconia and titania, noncorrosive materials such as fluororesin like polytetrafluoroethylene, and the like can be used. These can be used with one kind solely or two or more kinds in combination depending on the structure and shape of closed introducing section of the inventive appliance. For example, when using two-way cock as the closed introducing section, a combination of glass for the basic portion and fluororesin such as polytetrafluoroethylene for the cock portion, or the like is also used.

The material of an area not contacting with decomposition gas of the sample in the closed introducing section of the inventive appliance is not particularly restricted, if the material can withstand to the heat of radiation from furnace, and, for example, various metals such as stainless steel, brass, iron and aluminum, various glasses such as quartz and hard glass, various resins such as polyethylene, polypropylene, polystyrene, PET, PBT, polyamide, polyimide, phenol resin, fluororesins like polytetrafluoroethylene etc. various rubbers such as silicone rubber, NBR, chloroprene rubber and butyl rubber, and the like can be used.

It is preferable to separate the closed introducing section of the inventive appliance from furnace to some extent to suppress the effect of the heat of radiation from furnace. The distance cannot be determined sweepingly because of being different depending on the temperature of furnace, and may be determined taking the temperature of furnace, distance between furnace and closed introducing section and material of closed introducing section into account. For example, when using resin for the material of closed introducing section, the temperature of closed introducing section may be made not to exceed around 70° C., and, when the temperature of furnace is 600° C., the distance may be made to separate 3 cm or more. As exemplified, the distance may be determined appropriately taking the temperature of furnace, material of each section and distance into account. Moreover, when using more heat-resistant material such as quartz for the material of closed introducing section, it is possible to implement under conditions wherein the temperature of closed introducing section is higher.

The connecting form of closed introducing section to the heating section of the inventive appliance is not particularly restricted, provided that, even if the inner pressure inside the appliance may somewhat fluctuate during treatment of sample, the connection can be achieved leaklessly, and, for example, ground joint, screw, O-ring etc. mentioned. Here, the shape of O-ring is not particularly restricted and, in short, it is only necessary to have a circular hole at central portion and to be able to connect the closed introducing section to the heating section.

The method for introducing the absorbing liquid into the closed introducing section of the inventive appliance is not particularly restricted, provided that, even if the inner pressure may somewhat fluctuate, the absorbing liquid can be introduced without causing the leak, and such methods that cock or valve is used to close and it is opened and shut an introducing absorbing liquid, that packing or septum is used to close and needle pipe is used to introduce absorbing liquid, and the like can be mentioned. Moreover, the material of needle pipe to inject the absorbing liquid is not particularly restricted, provided that it is hard to be corroded with combustion gas and absorbing liquid and has sufficient strength and stainless steel, stainless steel with surface-inactivating treatment such as silica coating, and the like can be mentioned.

The heating temperature and heating time on decomposing the sample by using the inventive appliance is not particularly restricted, if the conditions allow to completely decompose the sample, but conditions of preferably not lower than 600° C. and not shorter than 3 minutes, more preferably not lower than 1000° C. and not shorter than 3 minutes are suitable. In particular, for a fire-resistant sample etc. containing high level of ash, heating over 1000° C. is preferable.

For setting up the sample in the inventive appliance, such methods that a vessel made of noncorrosive material such as platinum boat, ceramic boat, quartz boat or hard glass boat is used, that the sample is set up directly in the inventive appliance, and the like can be mentioned.

As the method for installing the inventive appliance in furnace, it is desirable to insert it horizontally or slantly into the furnace of heating device. More preferably, it is desirable to insert it horizontally or by slanting the closed introducing section downwards so that the decomposition gas of sample does not rise rapidly by convection to come out of furnace.

As for the oxygen to be filled up in the inventive appliance, such methods that pure oxygen, moist oxygen or oxygen mixed with inert gas such as nitrogen, helium or argon is filled up, and the like are mentioned.

The sample for pretreatment using the inventive appliance may or may not contain halogen and/or sulfur therein, and it is only necessary to determine depending on the purpose. When halogen and/or sulfur are contained in the sample, the inventive appliance can be used for quantitative determination of the content of halogen and/or sulfur in sample. Here, the contents of halogen and/or sulfur in sample mean that compound contained in sample may be single compound or a mixture of two or more compounds, and, in the case of single compound, compound contained therein can also be identified by comparing with the theoretical content of halogen and/or sulfur presumable from the structure of that compound.

The components in sample may or may not contain organics, and, when organics are contained, the organics are heated and burned by the inventive method, which is more effective. The sample is heat-decomposed by the inventive method, thereby the analyzed components are mineralized. The analyzed components are one or more kinds selected from a group consisting of halogen and sulfur, and, despite that the testing component(s) is solely one kind of halogen and sulfur or are two or more kinds, it(they) can be pretreated by the inventive method allowing to be submitted to the analysis.

Moreover, the inventive method can also be used to identify that one or more kinds of halogen and sulfur are not contained in the sample. In this case, it is possible to identify when neither halogen nor sulfur is contained in the sample and also to identify that either of particular halogen and sulfur is not contained in the sample. On that identification, while depending on the analytical method used, it is judged usually that it(they) is(are) not contained, if being not recognized within the sensitivity of that analytical method.

Moreover, the sample heat-decomposed by the inventive method is next submitted to the measurement of halogen and/or sulfur being the testing components. At this time, the analytical sample which may sometimes contain the testing components is prepared by introducing the absorbing liquid into the inventive appliance.

Here, the absorbing liquid to be used in the inventive method is not particularly restricted, if it can quantitatively dissolve the gas etc. containing halogen and sulfur originating from the heat-decomposed sample and keep them in a single form. For example, solution containing solely one kind, combined solution of arbitrary two or three kinds of hydrogen peroxide solution, hydrazine hydrate solution, aqueous solution of alkali metal hydroxide such as sodium hydroxide or potassium hydroxide, alkali solution such as aqueous ammonia, and the like, or pure water can be used. Thereamong, from the simplicity, it is preferable to use solely one kind of hydrogen peroxide solution, hydrazine solution, alkali solution and pure water as the absorbing liquid, and, for more highly exerting the effect as an absorbing liquid, it is preferable to use combination of arbitrary two kinds of hydrogen peroxide solution, hydrazine hydrate solution and alkali solution as the absorbing liquid.

In addition, upon using the absorbing liquid, it is also possible to select the type depending on the kind of halogen and sulfur to be analyzed after implementing the inventive pretreatment method. For example, when analyzing fluorine as a halogen, only pure water may be used, and, when analyzing chlorine, bromine or iodine as a halogen, it is preferable to use hydrogen peroxide solution or hydrazine hydrate solution to reduce halogen molecule gas generating after combustion, to which alkali solution can be added, if need be, when analyzing sulfur, hydrogen peroxide is preferably used to oxidize sulfur oxides generating after combustion, to which hydrazine hydrate solution or alkali solution can also be added, if need be. Further, for a compound having two or more kinds of these halogen and sulfur, the type of absorbing liquid may be selected appropriately depending on the composition of that compound.

On the other hand, when inorganic components such as alkali metal exist in the sample, halogen and sulfur originating from sample are often caught by this metal component as, for example, sodium chloride or iron sulfate, hence an absorbing liquid that can dissolve this caught component, too, is preferable.

Moreover, after introduction of absorbing liquid, the absorbing liquid contacts with the components originating from the heat-decomposed sample to absorb them into the absorbing liquid. At this time, it is possible to shorten the time by applying vibration etc. to appliance to increase the absorbing speed. As for the methods for vibration, any method of manual shaking, automated treatment with suitable device, and the like may be used.

The pretreated absorbed liquid thus obtained can be used as a sample for quantitative analysis and, as the methods for quantitative analysis, ion chromatographic method, titration method, colorimetric method, ion electrode method, etc. are mentioned.

Moreover, after the treatment as describe above, the inventive appliance can also be used again for the treatment of another sample after washing.

Examples of the inventive appliance comprising each section as described are shown in FIG. 1, FIG. 2, FIG. 3, FIG. 4 and FIG. 5. In following, the inventive appliance will be illustrated more concretely using figures. Besides, in the figures, mark showing each section is shown as a common number.

FIG. 1 is a schematic diagram of cross section of the inventive appliance in the axial direction. In FIG. 1, number 1 is an example using quartz tube with one side closed and other side having interchangeable ground joint 2. In place of this quartz tube 1, those made of said materials such as hard glass tube and alumina ceramic tube can also be used. To this interchangeable ground joint 2, absorbing liquid-introducing section made of hard glass etc. and provided with two-way cock 3 and absorbing liquid reservoir 4 is connected. On actual pretreatment, after oxygen and sample were set up in the quartz tube 1, two-way cock 3 is closed, heat-decomposition is performed followed by cooling, then absorbing liquid is accommodated in the absorbing liquid reservoir 4, and two-way cock 3 is opened to introduce the absorbing liquid into tube for use.

Figure 2:
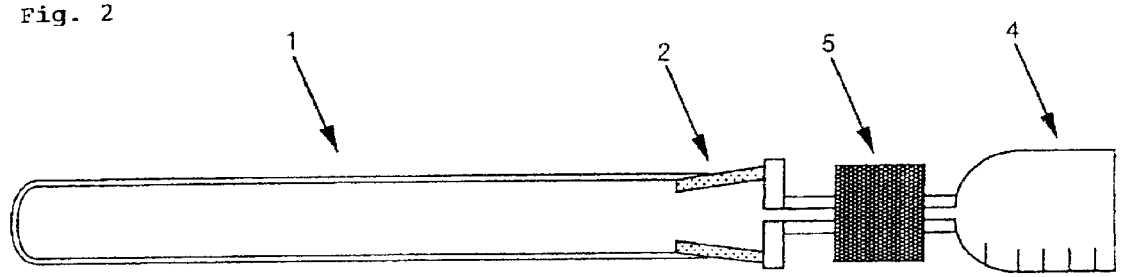
FIG. 2 is a schematic diagram of cross section of the inventive appliance in the axial direction.

FIG. 2 is a schematic diagram of cross section of the inventive appliance in the axial direction. In FIG. 2, numeral 1 is an example using quartz tube with one side closed and other side having interchangeable ground joint 2. To this interchangeable ground joint 2, absorbing liquid-introducing section as described above, made of hard glass etc. and provided with absorbing liquid reservoir 4 and solenoid valve 5 is connected. On actual pretreatment, operation may be made similarly to the case of appliance shown in FIG. 1.

Figure 3:
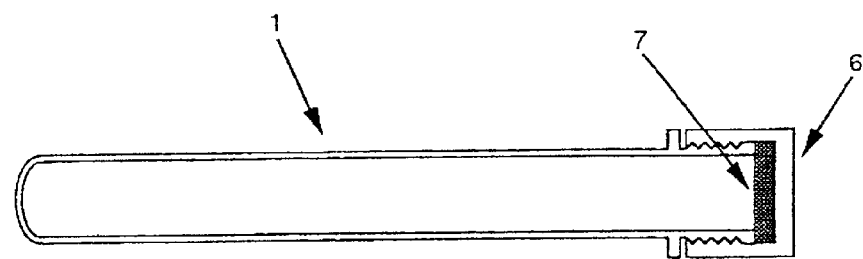
FIG. 3 is a schematic diagram of cross section of the inventive appliance in the axial direction.

FIG. 3 is a schematic diagram of cross section of the inventive appliance in the axial direction. In FIG. 2, numeral 1 is an example using quartz tube with one side closed and other side having thread ridge. A screw cap 6 fitted accurately to this thread ridge is connected to the quartz tube 1, interposing a septum 7 made of NBR rubber and stretched with Teflon membrane, the side of Teflon being directed to the inside of tube. On actual pretreatment, the absorbing liquid is injected with needle pipe from a small hole opened at the upper portion of screw cap 6, piercing through the septum 7 for use.

Figure 4:
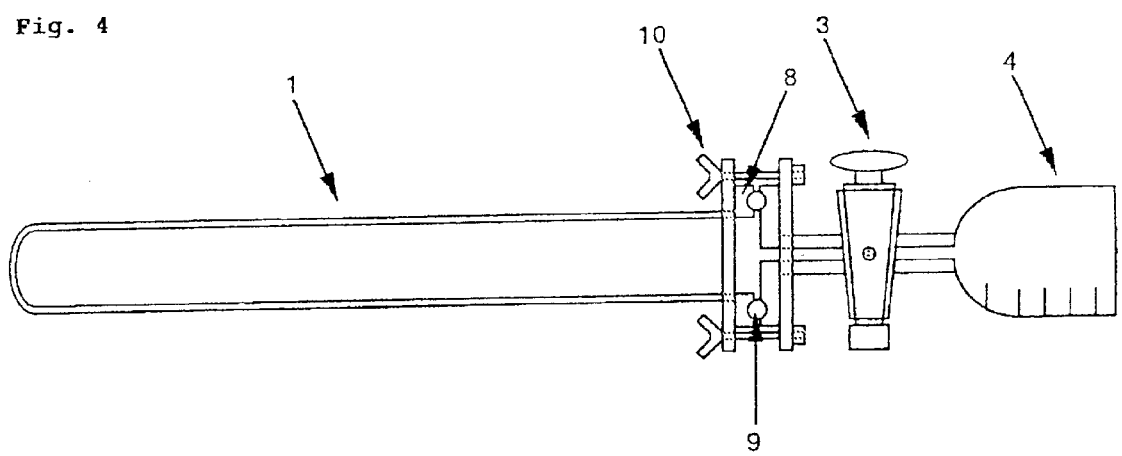
FIG. 4 is a schematic diagram of cross section of the inventive appliance in the axial direction.

FIG. 4 is a schematic diagram of cross section of the inventive appliance in the axial direction. In FIG. 4, numeral 1 is an example using quartz tube with one side closed and other side having O-ring receiver 8. To this O-ring receiver 8, the absorbing liquid-introducing section made of hard glass and provided with absorbing liquid reservoir 4 and two-way cock 3 is connected via O-ring 9, which is tightened with clamp 10 for use.

Figure 5:
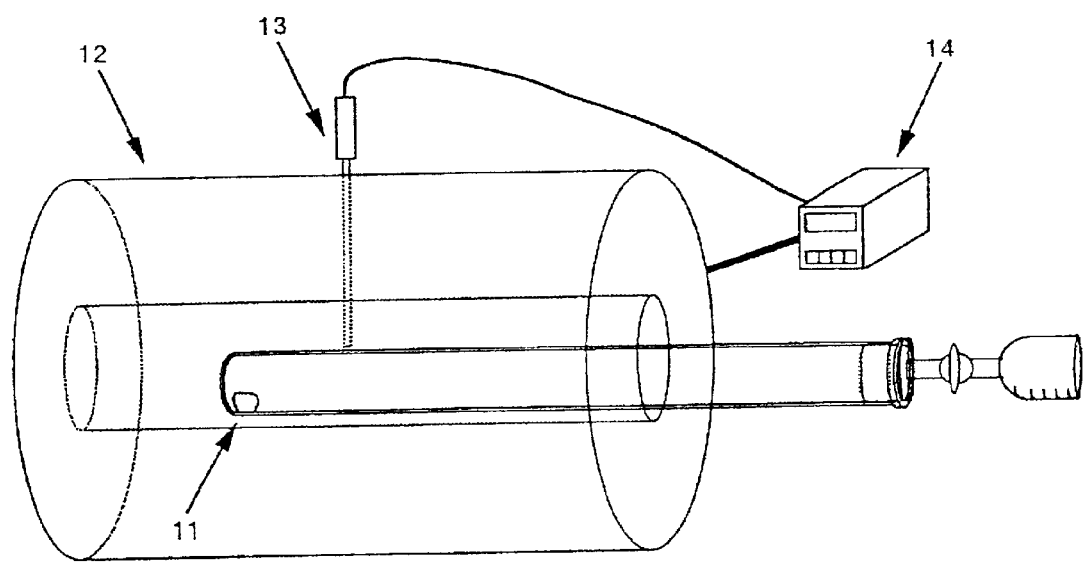
FIG. 5 is a schematic diagram at the time of heating with circular electric furnace by using the inventive appliance.

FIG. 5 is a schematic diagram at the time of heating with circular electric furnace by using the inventive appliance. The inventive appliance with sample 11 placed therein is placed in the circular electric furnace 12 and, while measuring the temperature with thermocouple 13, temperature is controlled with temperature-controlling device to heat, thereby allowing to heat-decompose the sample 11 in the inventive appliance.

Next, the inventive device will be illustrated in detail.

The inventive device comprises a device for the inventive pretreatment of sample, consisting of appliance-installing section for installing the inventive appliance, heating means to heat-decompose the sample in the inventive appliance, cooling means to cool the inventive appliance after heat-decomposition of sample in the inventive appliance, injecting means to inject the absorbing liquid into the inventive appliance after cooling, mixing means to stir and/or shake for making the absorbing liquid in the inventive appliance uniform and moving means to reversibly move the inventive appliance from appliance-installing section to any of cooling means, injecting means and mixing means and from there to any of others thereamong. Further, in addition to this pretreatment device of sample, sampling means to sample part of the absorbed liquid in the inventive appliance and to move to analyzing means, and the inventive analytical device having analyzing means to analyze the testing components in absorbed liquid are also within a range of the invention.

The material of appliance-installing section to be used for the inventive appliance is not particularly restricted, and it is only necessary to have a structure that holds the inventive appliance one by one, and that can move the inventive appliance with the measuring sample accommodated therein by moving means shown below after start of pretreatment, or can install the inventive appliance to its appliance-installing section by moving means after pretreatment.

The heating means to be used in the inventive device is not particularly restricted, provided that it has a capacity capable of heat-decomposing the measuring sample as described above and that one or a plurality of the inventive appliances are moved by moving means shown below after start of pretreatment to set up the heating section of the inventive appliance. As a heating device with such heating means, for example, electric furnace easy to control the heating temperature is used preferably and, as for the shape thereof, it is preferable to be a furnace shaped complementarily with the shape of heating section of the inventive appliance.

The cooling means to be used in the inventive device is not particularly restricted, if it has a mechanism that, after heat-decomposing the measuring sample in the inventive appliance by said heating means, the inventive appliance is taken out from the heating means by moving means, and thereafter the heated inventive appliance is held above this cooling device to allow to cool to a temperature as low as the room temperature, but, for avoiding the failure of the inventive appliance due to rapid cooling, air cooling with fan, air shower or the like is preferable. As for the distance between the inventive appliance and the cooling means during cooling, it is only necessary to be a distance capable of rapidly cooling the heated inventive appliance, depending on the size of cooling means, exhaust capacity of air etc. and the like. Moreover, without using the device with such cooling mechanism, the inventive appliance may be allowed to stand for cooling by holding it as it is after taken out the heated inventive appliance by moving means.

The injecting means to be used in the inventive device is not particularly restricted, if it can hold the inventive appliance cooled by said cooling means and inject the absorbing liquid without leak of gas of the testing components produced by decomposition of sample set up in the inventive appliance. For example, when using the inventive appliance that opens and shuts the closed introducing section closed with cock or valve on introduction of the absorbing liquid, a mechanism for injecting under pressure from tube connected to cock or valve using various pumps etc., a mechanism for sucking the absorbing liquid from tube connected to cock or valve, making the inside negative pressure by cooling the inventive appliance, and the like can be used. Moreover, when using the inventive appliance that is closed with packing or septum and introduces the absorbing liquid with needle pipe, a mechanism for injecting under pressure from tube connected to needle pipe using various pumps etc. and the like can be used. Thereamong, preferably, in the case of appliance comprising the closed introducing section with packing or septum to introduce the absorbing liquid with needle pipe as a mechanism for introducing the absorbing liquid for absorbing the testing components from outside, an absorbing liquid-injecting mechanism comprising needle pipe, motor buret, valve with actuator, moving mechanism of needle pipe and washing place, wherein the needle pipe is pierced through the packing or septum of the inventive appliance by moving mechanism, the absorbing liquid is introduced by switching the valve with actuator and working the motor buret, and then needle pipe is moved to the washing place kx moving mechanism to wash the contaminated needle pipe, is preferable for use.

The mixing means to stir and/or shake for making the absorbing liquid in the inventive appliance uniform to be used in the inventive device is to mix gaseous halogen and/or sulfur being the testing components generated by decomposition of the inner measuring sample during heating of the inventive appliance, with the absorbing liquid injected into the inventive appliance by said injecting means, and to make the concentration of the testing components being dissolved into the absorbing liquid and existing in that solution uniform, and is not particularly restricted, if it can wash out the wall of vessel and all with absorbing liquid so that all including the testing components stuck onto the wall of vessel are taken into the absorbing liquid and can make the absorbed liquid in the inventive appliance uniform. For example, a mechanism for rotating the inventive appliance installed horizontally centering around axis, a mechanism for moving the inventive appliance installed vertically up and down centering around axis, a mechanism for rotating the inventive appliance installed vertically in parallel with axis, and the like can be mentioned. Thereamong, preferably, one with a stirring mechanism for reciprocating the inventive appliance installed horizontally in the axial direction while rotating centering around axis is preferable for use.

The moving means that supports the inventive appliance and moves it reversibly to each portion of appliance-installing section, heating means, cooling means, injecting means, mixing means or the like to be used in the inventive deice is not particularly restricted, if it has a mechanism for transporting the inventive appliance while holding it. Among the moving means with such mechanism, it is preferable to equip a mechanical hand that holds the inventive appliance and to utilize one or more of cross type motor robot, cross type multiaxial motor robot, multijoint type robot, belt conveyer, air cylinder, hydraulic cylinder, etc. Further, it is preferable to use cross type motor robot with mechanical hand or cross type motor robot with mechanical hand and axis for rotating this.

With a device provided with such each means, the inventive pretreatment device for performing the pretreatments such as heat-decomposition of sample and dissolution of analyzed components producing by heat-decomposition into absorbing liquid is constituted.

Furthermore, by combining an analytical device provided with sampling means shown below with this inventive pretreatment device, the inventive analytical device is constituted.

Namely, the sampling means for sampling part of the absorbed liquid inside the inventive appliance and moving to the analyzing means to be used in the inventive device is not particularly restricted, if it can sample part or all of the absorbed liquid from absorbed liquid with the analyzed components dissolved uniformly in the inventive appliance by said mixing means. For example, a mechanism for sucking the absorbed liquid by inserting the needle pipe into the inventive appliance, a mechanism for discharging the absorbed liquid by pressurizing the inside, and the like can be mentioned.

The analytical device with analyzing means to analyze the testing components in the absorbed liquid to be used in the inventive device is not particularly restricted, if it can analyze the testing components by interlocking with the mechanism for sampling the absorbed liquid from the inventive appliance and feeding. For example, ion chromatograph, automatic titrator, automatic spectrophotometer, ion meter, etc. are mentioned.

In following, said each section to be used in the inventive pretreatment device and the inventive analytical device will be illustrated more concretely, referring to drawings.

Figure 6:
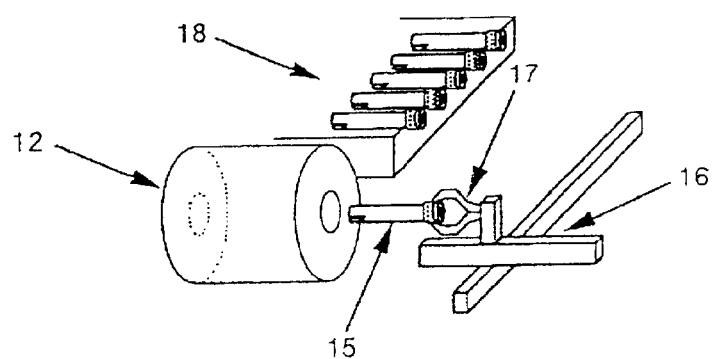
FIG. 6 is a schematic diagram of the inventive pretreatment device.

FIG. 6 is a schematic diagram of the inventive pretreatment device. In FIG. 6, numeral 15 is the inventive appliance and, by cross type motor robot 16 and mechanical hand 17, the inventive appliance 15 is transported from appliance-installing section 18 to circular electric furnace 12.

Figure 7:
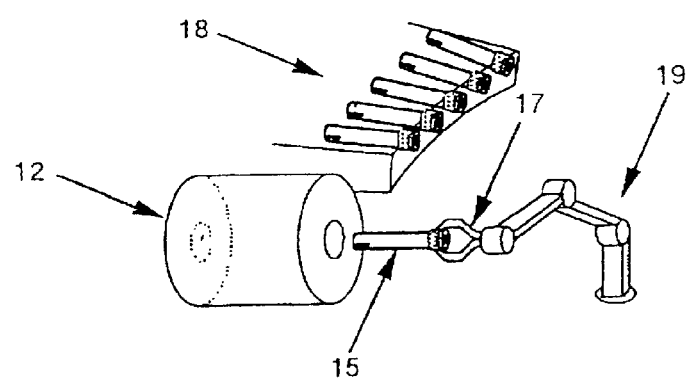
FIG. 7 is a schematic diagram of the inventive pretreatment device.

FIG. 7 is a schematic diagram of the inventive pretreatment device. In FIG. 7, numeral 15 is the inventive appliance and, by multijoint type motor robot 19 and mechanical hand 17, the inventive appliance 15 is transported from appliance-installing section 18 to circular electric furnace 12.

Figure 8:
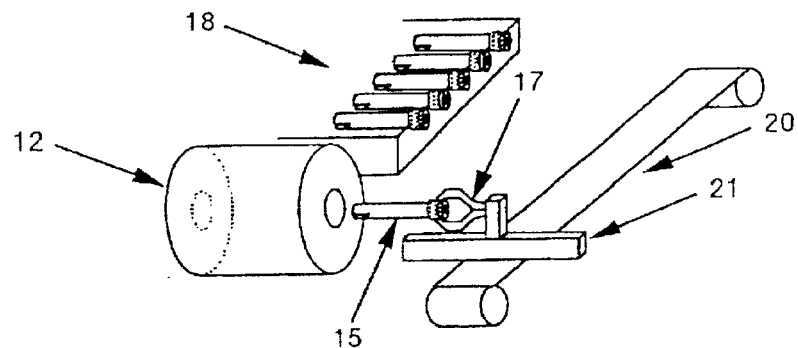
FIG. 8 is a schematic diagram of the inventive pretreatment device.

FIG. 8 is a schematic diagram of the inventive pretreatment device. In FIG. 8, numeral 15 is the inventive appliance and, by belt conveyer 20, air cylinder 21 and mechanical hand 17, the inventive appliance 15 is transported from appliance-installing section 18 to circular electric furnace 12.

Figure 9:
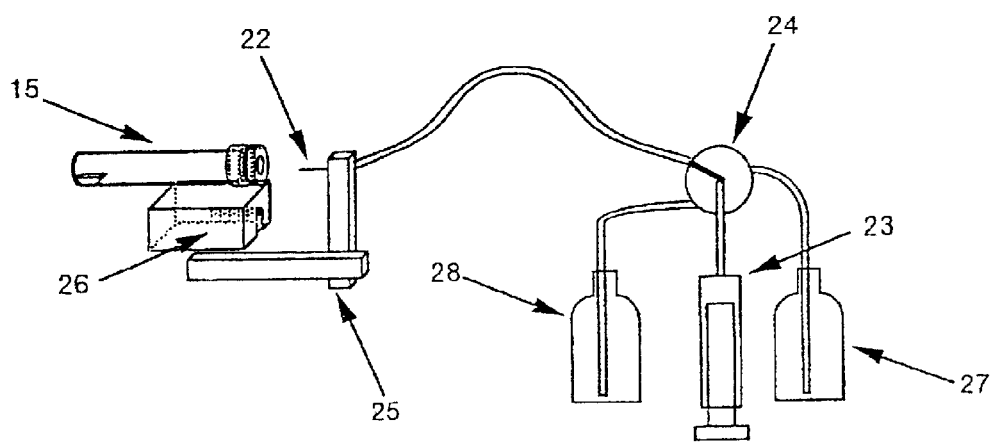
FIG. 9 is a schematic diagram of the mechanism for injecting the absorbing liquid into the inventive appliance.

FIG. 9 is a schematic diagram of the mechanism for injecting the absorbing liquid into the inventive appliance. In FIG. 9, numeral 15 is the inventive appliance with packing or septum, numeral 22 is needle pipe, numeral 23 is motor buret, numeral 24 is valve with actuator, numeral 25 is moving mechanism of needle pipe and numeral 26 is washing place. The needle pipe 22 is pierced through packing or septum of the inventive appliance 15 by moving mechanism 25, and, after injected the absorbing liquid in absorbing liquid reservoir 27 by switching valve 24 with actuator and working motor buret 23, the needle pipe 22 is moved to washing place 26 by moving mechanism 25 to wash the contaminated needle pipe with washing liquid in the washing liquid reservoir 28.

Further, in the mechanism for injecting the absorbing liquid into the inventive appliance, it is also possible to inject as follows.

The inventive appliance is connected to cock (solenoid valve) and the cock is connected to motor buret accommodated with absorbing liquid via tube. The absorbing liquid is injected to the inventive appliance by opening cock and working motor buret.

The inventive appliance is connected to cock and the cock is connected to plunger pump accommodated with absorbing liquid via tube. The absorbing liquid is injected to the inventive appliance by opening cock and working plunger pump.

The inventive appliance is connected to valve and the valve is connected to motor buret accommodated with absorbing liquid via tube. The absorbing liquid is injected to the inventive appliance by switching valve to connect the motor buret to the inventive appliance and working motor buret.

The inventive appliance is connected to valve and the valve is connected to absorbing liquid reservoir accommodated with absorbing liquid via tube. The absorbing liquid is injected to the inventive appliance by cooling the inventive appliance to make the inside of appliance negative pressure and switching valve to connect the absorbing liquid reservoir to the inventive appliance.

Figure 10:
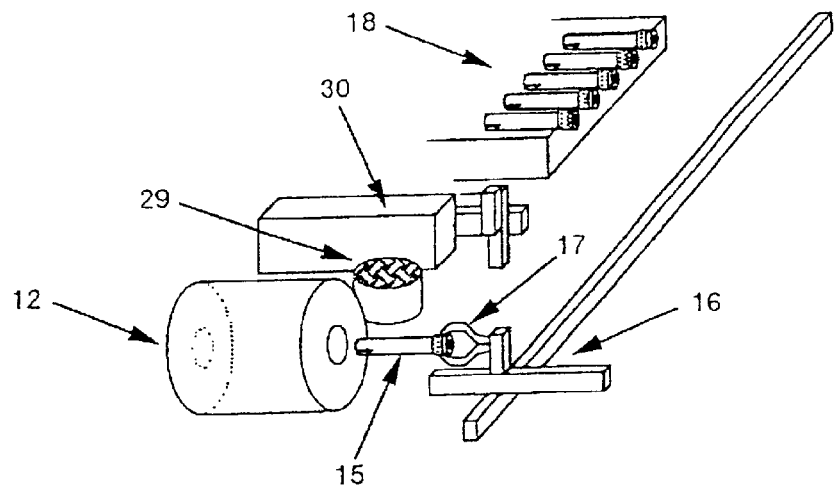
FIG. 10 is a schematic diagram of the inventive pretreatment device.

FIG. 10 is a schematic diagram of the inventive pretreatment device. In FIG. 10, numeral 15 is the inventive appliance and, by cross type motor robot 16 and mechanical hand 17, the inventive appliance 15 is transported from appliance-installing section 18 to circular electric furnace 12. Thereafter, the heated inventive appliance 15 is transported to fan 29 to be cooled and then transported to absorbing liquid-injecting mechanism 30 to receive injection of absorbing liquid.

Figure 11:
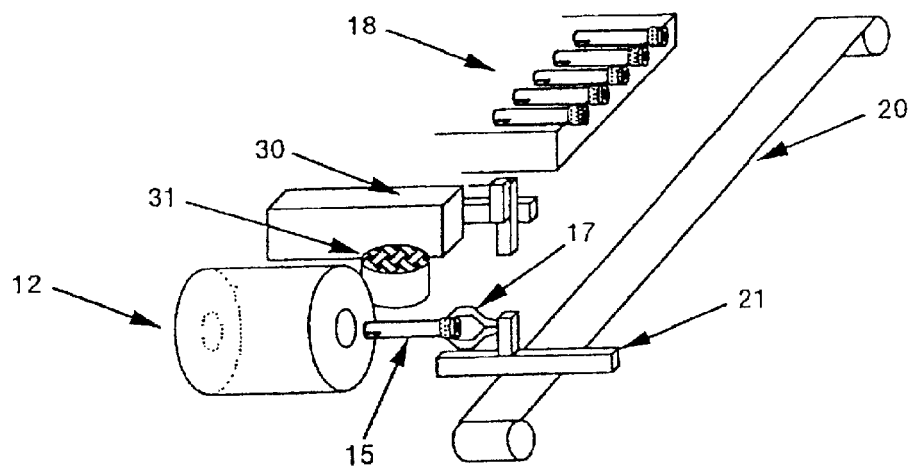
FIG. 11 is a schematic diagram of the inventive pretreatment device.

FIG. 11 is a schematic diagram of the inventive pretreatment device. In FIG. 11, numeral 15 is the inventive appliance and, by belt conveyer 20, air cylinder 21 and mechanical hand 17, the inventive appliance 15 is transported from appliance-installing section 18 to circular electric furnace 12. Thereafter, the heated inventive appliance 15 is transported to air shower 31 to be cooled and then transported to absorbing liquid-injecting mechanism 30 to receive injection of absorbing liquid.

Figure 12:
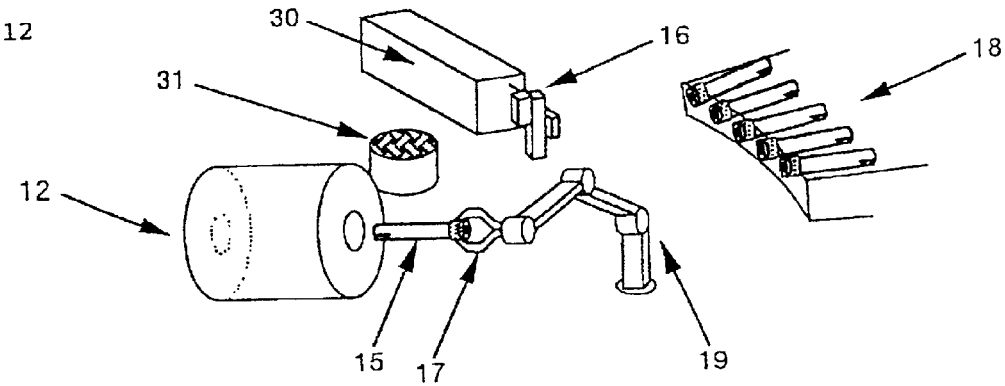
FIG. 12 is a schematic diagram of the inventive pretreatment device.

FIG. 12 is a schematic diagram of the inventive pretreatment device. In FIG. 12, numeral 15 is the inventive appliance and, by multijoint type motor robot 19 and mechanical hand 17, the inventive appliance 15 is transported from appliance-installing section 18 to circular electric furnace 12. Thereafter, the heated inventive appliance 15 is transported to air shower 31 to be cooled and then transported to absorbing liquid-injecting mechanism 30 to receive injection of absorbing liquid.

Figure 13:
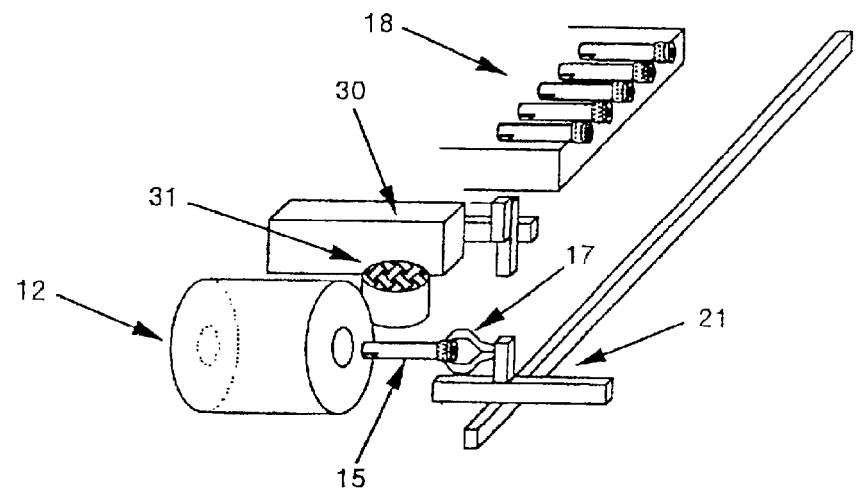
FIG. 13 is a schematic diagram of the inventive pretreatment device.

FIG. 13 is a schematic diagram of the inventive pretreatment device. In FIG. 13, numeral 15 is the inventive appliance and, by air cylinder 21 and mechanical hand 17, the inventive appliance 15 is transported from appliance-installing section 18 to circular electric furnace 12. Thereafter, the heated inventive appliance 15 is transported to air shower 31 to be cooled and then transported to absorbing liquid-injecting mechanism 30 to receive injection of absorbing liquid.

Figure 14:
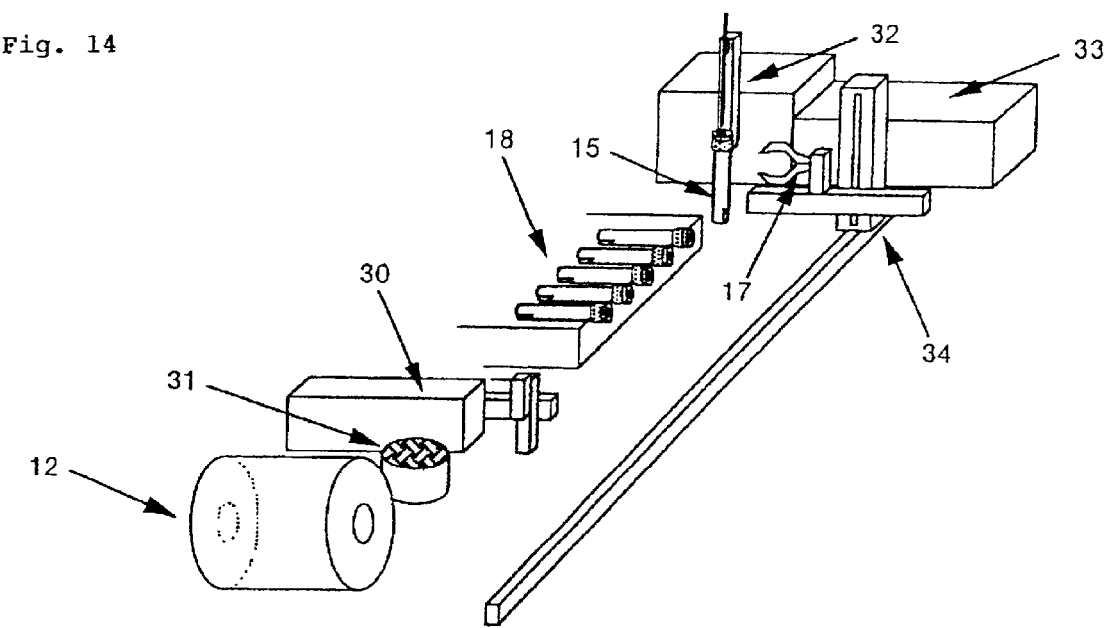
FIG. 14 is a schematic diagram of the inventive analytical device.

FIG. 14 is a schematic diagram of the inventive analytical device. In FIG. 14, numeral 15 is the inventive appliance and, by cross type multiaxial motor robot 34 and mechanical hand 17, the inventive appliance 15 is transported from appliance-installing section 18 to circular electric furnace 12. Thereafter, the heated inventive appliance 15 is transported to air shower 31 to be cooled and then transported to absorbing liquid-injecting mechanism 30 to receive injection of absorbing liquid. And, after sufficiently stirred the inventive appliance 15 by cross type multiaxial motor robot 34 and mechanical hand 17, port or all of absorbed liquid in the inventive appliance 15 are sampled with autosampler 32 and infected into ion chromatographic deice 33 to analyze the testing components.

Figure 15:
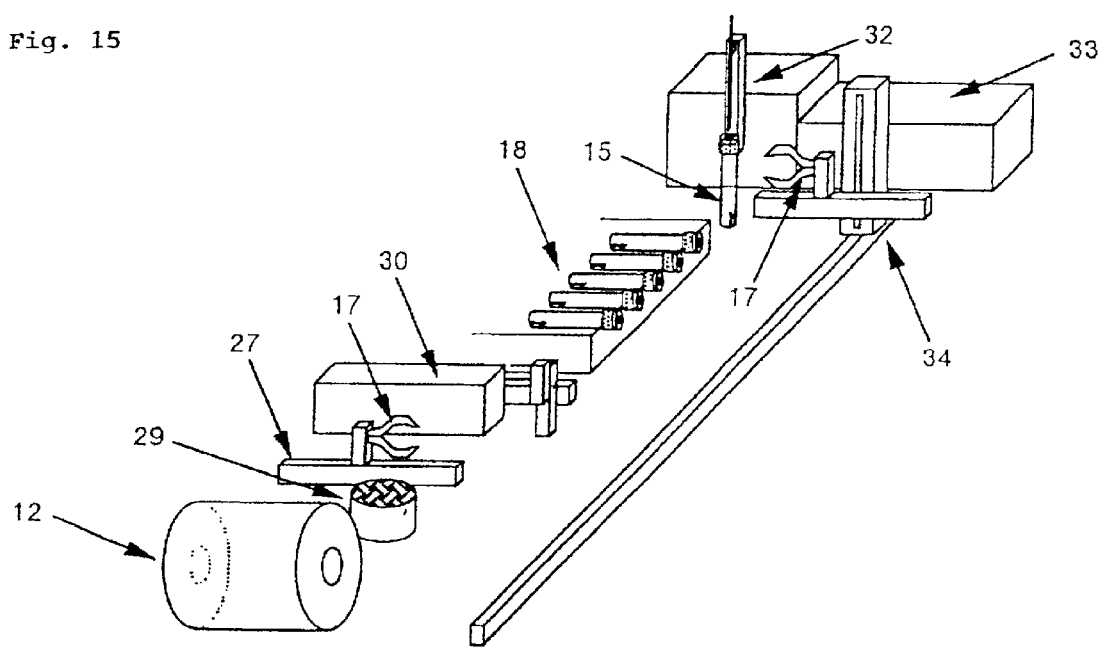
FIG. 15 is a schematic diagram of the inventive analytical device.

FIG. 15 is a schematic diagram of the inventive analytical device. In FIG. 15, numeral 15 is the inventive appliance and, by cross type multiaxial motor robot 34 and mechanical hand 17, the inventive appliance 15 is transported from appliance-installing section 18 to circular electric furnace 12. Thereafter, the heated inventive appliance 15 is transported to fan 29 to be cooled and then transported to absorbing liquid-injecting mechanism 30 to receive injection of absorbing liquid. And, after sufficiently stirred the inventive appliance 15 with stirring absorbing mechanism comprising uniaxial motor robot 35 and mechanical hand 17, port or all of absorbed liquid are sampled with autosampler 32 and injected into ion chromatographic device 33 to analyze the testing components. Besides, as for the stirring absorbing mechanism, a stirring absorbing mechanism comprising air cylinder or belt conveyer and mechanical hand may be used.

By appropriately disposing each means to be used in the inventive device as above, the inventive pretreatment device or the inventive analytical device is constituted.

Moreover, on the actual pretreatment or analysis, each section in these inventive devices may be operated separately by each section, but can be operated under control by information processing means such as computer so as to become the routine aforementioned.

The inventive appliance, inventive method and inventive device as described above are used suitably for the quality control of organics to be manufactured or used, identification of compounds, grasp of elemental compositions, and the like in all industries such as petroleum, chemicals, medicines, foods, semiconductor and papermaking.

In following, the invention will be illustrated in detail based on the examples, but the invention is not confined only to these examples.

Besides, the results etc. obtained in following examples 1 through 20 are collectively shown, respectively; type of sample, quantity of sample, theoretical consumption amount of oxygen, amount of oxygen at heating section of the inventive appliance and ratio of amount of oxygen at heating section to theoretical consumption amount of oxygen in Table 1; material of heating section, inner diameter of heating section, length on injection of sample into furnace, heating temperature, heating time, material of sample boat, type of absorbing liquid used and angle on slating sample in Table 2; contents of halogen and sulfur derived theoretically from sample (theoretical value), contents of halogen and sulfur obtained as a result (observed value) and recovery rate being a ratio therebetween (observed value/theoretical value) in Table 3.

TABLE 1

(Sample)

| Example No. | Type of Sample | Quantity of sample (mg) | Theoretical amount of oxygen (ml) | Amount of oxygen at heating section (ml) | Amt. of oxygen at heating section/ theoretical amt. of oxygen |
|---|---|---|---|---|---|
| Example 1 | S-benzylthiuronium chloride | Ca.5 | 8.15 | 40.2 | 4.93 |
| Example 2 | Fire-resistant ABS | Ca.5 | 9.60 | 40.2 | 4.19 |
| Example 3 | S-benzylthiuronium chloride | 4.790 | 7.82 | 40.2 | 5.14 |
| Example 4 | S-benzylthiuronium chloride | 2.902 | 4.74 | 15.7 | 3.31 |
| Example 5 | S-benzylthiuronium chloride | 3.601 | 5.88 | 15.7 | 2.67 |
| Example 6 | S-benzylthiuronium chloride | 7.712 | 12.6 | 40.2 | 3.19 |
| Example 7 | S-benzylthiuronium chloride | 2.282 | 3.72 | 11.8 | 3.17 |
| Example 8 | S-benzylthiuronium chloride | 4.885 | 7.97 | 40.2 | 5.04 |
| Example 9 | S-benzylthiuronium chloride | 4.915 | 8.02 | 40.2 | 5.01 |
| Example 10 | S-benzylthiuronium chloride | 2.486 | 4.06 | 15.7 | 3.87 |
| Example 11 | S-benzylthiuronium chloride | 5.302 | 8.65 | 57.2 | 8.61 |
| Example 12 | S-benzylthiuronium chloride | 5.118 | 8.35 | 40.2 | 4.81 |
| Example 13 | S-benzylthiuronium chloride | 4.457 | 7.27 | 40.2 | 5.53 |
| Example 14 | S-benzylthiuronium chloride | 5.339 | 8.71 | 40.2 | 4.62 |
| Example 15 | S-benzylthiuronium chloride | 4.754 | 7.76 | 40.2 | 5.18 |
| Example 16 | Fire-resistant ABS | 5.080 | 9.74 | 40.2 | 4.13 |
| Example 17 | p-chlorobenzoic acid | 4.804 | 5.26 | 40.2 | 7.64 |
| Example 18 | S-benzylthiuronium chloride | 1.573 | 2.57 | 15.7 | 6.11 |
| Example 19 | S-benzylthiuronium chloride | 4.900 | 8.00 | 40.2 | 5.03 |
| Example 20 | o-iodobenzoic acid | 5.370 | 3.71 | 40.2 | 10.8 |

TABLE 2

(Appliance plus conditions)

| Example No. | Material of heating section | Inner diameter of heating section (mm) | Inserting length into furnace (cm) | Heating temperature (°C.) | Heating time (min) | Material of sample boat | Type of absorbing liquid | Slanting angle (deg.) |
|---|---|---|---|---|---|---|---|---|
| Example 1 | Quartz | 16 | 20 | 1000 | 5 | Platinum | NaOH + $H_2O_2$ | 0 |
| Example 2 | Quartz | 16 | 20 | 1000 | 5 | Platinum | NaOH + $H_2O_2$ | 0 |
| Example 3 | Quartz | 16 | 20 | 800 | 3 | Platinum | NaOH + $H_2O_2$ | 0 |
| Example 4 | Quartz | 10 | 20 | 1000 | 5 | Platinum | NaOH + $H_2O_2$ | 0 |
| Example 5 | Quartz | 10 | 20 | 1000 | 5 | Platinum | NaOH + $H_2O_2$ | 0 |
| Example 6 | Quartz | 16 | 20 | 1000 | 5 | Platinum | NaOH + $H_2O_2$ | 0 |
| Example 7 | Quartz | 10 | 15 | 1000 | 5 | Platinum | NaOH + $H_2O_2$ | 0 |
| Example 8 | Quartz | 16 | 20 | 1000 | 5 | Quartz | NaOH + $H_2O_2$ | 0 |
| Example 9 | Quartz | 16 | 20 | 1000 | 5 | Ceramic | NaOH + $H_2O_2$ | 0 |
| Example 10 | Quartz | 10 | 20 | 1000 | 5 | Direct set up | NaOH + $H_2O_2$ | 0 |
| Example 11 | Quartz | 27 | 10 | 1000 | 5 | Quartz | NaOH + $H_2O_2$ | 0 |
| Example 12 | Quartz | 16 | 20 | 1000 | 5 | Platinum | NaOH + $H_2O_2$ | 0 |
| Example 13 | Quartz | 16 | 20 | 1000 | 5 | Platinum | NaOH + $H_2O_2$ | 0 |
| Example 14 | Quartz | 16 | 20 | 1000 | 5 | Platinum | NaOH + $H_2O_2$ | 0 |
| Example 15 | Quartz | 16 | 20 | 1000 | 5 | Platinum | NaOH + $H_2O_2$ | 30 |
| Example 16 | Quartz | 16 | 20 | 1000 | 5 | Platinum | NaOH + $NH_2NH_2$ | 0 |
| Example 17 | Quartz | 16 | 20 | 1000 | 5 | Quartz | $H_2O$ | 0 |
| Example 18 | Hard glass | 10 | 20 | 600 | 30 | Hard glass | NaOH + $H_2O_2$ | 0 |
| Example 19 | Ceramic | 16 | 20 | 1000 | 5 | Platinum | NaOH + $H_2O_2$ | 0 |
| Example 20 | Quartz | 16 | 20 | 1000 | 5 | Platinum | NaOH + $NH_2NH_2$ + $H_2O_2$ | 0 |

TABLE 3

(Results)

| Example No. | Theoretical value (%) | Observed value (%) | Recovery rate (%) |
|---|---|---|---|
| Example 1 | Cl: 17.49<br>S: 15.82 | Cl: 17.46<br>S: 15.67 | Cl: 99.83<br>S: 99.05 |
| Example 2 | Br: 9.73 | Br: 9.62 | Br: 98.87 |
| Example 3 | Cl: 17.49<br>S: 15.82 | Cl: 17.52<br>S: 15.64 | Cl: 100.17<br>S: 98.86 |
| Example 4 | Cl: 17.49<br>S: 15.82 | Cl: 17.66<br>S: 15.79 | Cl: 100.97<br>S: 99.81 |
| Example 5 | Cl: 17.49<br>S: 15.82 | Cl: 18.04<br>S: 15.96 | Cl: 103.14<br>S: 100.88 |
| Example 6 | Cl: 17.49<br>S: 15.82 | Cl: 17.32<br>S: 15.70 | Cl: 99.03<br>S: 99.24 |
| Example 7 | Cl: 17.49<br>S: 15.82 | Cl: 17.32<br>S: 15.54 | Cl: 99.03<br>S: 98.23 |

TABLE 3-continued (Results)

| Example No. | Theoretical value (%) | Observed value (%) | Recovery rate (%) |
|---|---|---|---|
| Example 8 | Cl: 17.49 | Cl: 17.42 | Cl: 99.60 |
| | S: 15.82 | S: 15.74 | S: 99.49 |
| Example 9 | Cl: 17.49 | Cl: 17.31 | Cl: 98.97 |
| | S: 15.82 | S: 15.66 | S: 98.99 |
| Example 10 | Cl: 17.49 | Cl: 17.66 | Cl: 100.97 |
| | S: 15.82 | S: 15.79 | S: 99.81 |
| Example 11 | Cl: 17.49 | Cl: 17.45 | Cl: 99.77 |
| | S: 15.82 | S: 15.55 | S: 98.29 |
| Example 12 | Cl: 17.49 | Cl: 17.56 | Cl: 100.40 |
| | S: 15.82 | S: 15.65 | S: 98.93 |
| Example 13 | Cl: 17.49 | Cl: 17.32 | Cl: 99.03 |
| | S: 15.82 | S: 15.66 | S: 98.99 |
| Example 14 | Cl: 17.49 | Cl: 17.57 | Cl: 100.46 |
| | S: 15.82 | S: 15.79 | S: 99.81 |
| Example 15 | Cl: 17.49 | Cl: 17.28 | Cl: 98.80 |
| | S: 15.82 | S: 15.82 | S: 100.00 |
| Example 16 | Br: 9.73 | Br: 9.55 | Br: 98.15 |
| Example 17 | Cl: 22.64 | Cl: 22.00 | Cl: 97.17 |
| Example 18 | Cl: 17.49 | Cl: 17.90 | Cl: 102.34 |
| | S: 15.82 | S: 15.43 | S: 97.53 |
| Example 19 | Cl: 17.49 | Cl: 17.44 | Cl: 99.71 |
| | S: 15.82 | S: 15.77 | S: 99.68 |
| Example 20 | I: 15.17 | I: 15.09 | I: 99.47 |

Moreover, the values of detecting lower limit (detecting sensibility) of IC measurement are 0.05 µg/ml for fluorine (F$^-$), 0.05 µg/ml for chlorine (Cl$^-$), 0.1 µg/ml for bromine (Br$^-$), 0.3 µg/ml for iodine (I$^-$) and 0.1 µg/ml for sulfur (as SO$_4^{2-}$). In following examples, the contents of halogen and sulfur in sample determined by the detecting lower limit of IC measurement are 0.05% for fluorine, 0.05% for chlorine, 0.1% for bromine, 0.3% for iodine and 0.03% for sulfur, and the contents of elements not described in each example are below those described above. In addition, IC measurement was made by diluting the absorbed liquid to 50 ml, but, if diluting to 5 ml being one tenth, the detection limit for the contents of halogen and sulfur in sample will become one tenth of those above.

EXAMPLE 1

About 5 mg of S-benzylthiuronium chloride (from Kishida Kagaku Co.) were weighed out accurately into a platinum boat with length of 5 mm, width of 15 mm and height of 4 mm using microbalance M-3 from Metler Co., and inserted deep in a closed heat-decomposing appliance (length of tube: 30 cm, inner diameter of tube: 16 mm, outer diameter of tube: 18 mm) shown in FIG. 1. After injected oxygen, the appliance was stoppered at the absorbing liquid-introducing section. This closed heat-decomposing appliance was inserted horizontally as far as about 20 cm from the side of sample into a circular electric furnace (from Isuzu Seisakusho Co., attached with temperature controller EC5600 from Okura Electric Co.) heated to 1000° C. and heated for 5 minutes. Then, the closed heat-decomposing appliance was drawn out from the furnace, cooled, and injected with 2.5 ml of absorbing liquid comprising an aqueous solution of 0.04 mol/L sodium hydroxide and 24% by weight of hydrogen peroxide from two-way cock, followed by shaking, which was allowed to stand for 30 minutes. Thereafter, the inside of the closed heat-decomposing appliance including ground portion was washed with pure water and diluted to 50 ml to submit to IC measurement.

As for IC, CCPM (specified for resin) from Tosoh Corp. was used for pump, CM-8010 (electroconductivity detector) from Tosoh Corp. for detector, CO-8011 from Tosoh Corp. for column oven, SC-8020 from Tosoh Corp. for integrator, TSK gel IC-Anion-PwPEEK (4.6 mm I.D.×50 mm) from Tosoh Corp. for analytical column, and 1,3 mM potassium gluconate-1.3 mM borax-30 mM boric acid-5% acetonitrile-0.5% glycerol glycerine for mobile layer, and measurement was made under flow rate of 1.2 ml/mm, column temperature of 40° C. and sample injection volume of 100 µL. The calibration curve was prepared by appropriately diluting anion standard solution from Wako Pure Chemical Industries Ltd. to measure the absorbed liquid after decomposition of sample.

To the theoretical contents (% by weight) of 17.49% for Cl and 15.82% for S in 5-benzylthiuronium chloride, the average and relative standard deviations (RSD) on ten measurements (three appliances were use repeatedly four times, four times and two times for each appliance) were 17.46% (RJD=0.88%) for Cl and 15.67% (RSD=0.35%) for S.

Besides, in this example, the ratio of the amount of oxygen (=40.2 ml) at heating section to the theoretical amount of oxygen (=8.15 ml) required for complete combustion of S-benzylthiuronium chloride was 4.93.

EXAMPLE 2

Except that a fire-resistant ABS kneaded 100 parts of ABS (trade name JSR ABS10) from Japan Synthetic Rubber Co. with 26 parts of brominated epoxy resin flame retardant (trade name YDB-408) from Toto Kasei Co. and 8.7 parts of flame retardant Sb2O3 (trade name Flame Cut 610R) from Tosoh Corp. was used for the sample, sample was pretreated similarly to Example 1 to implement the IC measurement. As a result, to the content (% by weight) of 9.73% for Br in this substance determined from the quantity charged, the average and relative standard deviation on seen measurements (two appliances were used repeatedly five times and two times for each appliance) were 9.62% (RSD=1.53%).

EXAMPLE 3

Except that the temperature of furnace and the heating time were made to be 800° C. and 3 minutes, respectively, sample was pretreated similarly to Example 1 to implement the IC measurement. As a result, to the theoretical contents (% by weight) of 17.49% for Cl and 15.82% for S in S-benzylthiuronium chloride, 17.52% and 15.64% were obtained for Cl and S. respectively.

EXAMPLE 4

Except that the shape of the closed heat-decomposing appliance used in Example 1 was made to be length of tube of 30 cm, inner diameter of tube of 10 mm and outer diameter of tube of 12 mm and 2.902 mg of S-benzylthiuronium chloride were used, sample was pretreated similarly to Example 1 to implement the IC measurement. As a result, to the theoretical contents (% by weight) of 17.49% for Cl and 15.82% for S in S-benzylthiuronium chloride, 17.66% and 15.79% were obtained for Cl and S, respectively.

Besides, in this example, the ratio of the amount of oxygen (=15.7 ml) at heating section to the theoretical amount of oxygen (=4.74 ml) required for complete combustion of S-benzylthiuronium chloride was 3.31.

EXAMPLE 5

Except that 3.601 mg of S-benzylthiuronium chloride were used, sample was pretreated similarly to Example 4 to implement the IC measurement similarly to Example 1. As a result, to the theoretical contents (% by weight) of 17.49% for Cl and 15.82% for S in S-benzylthiuronium chloride, 18.04% and 15.96% were obtained for Cl and S, respectively.

Besides, in this example, the ratio of the amount of oxygen (=15.7 ml) at heating section to the theoretical amount of oxygen (=5.88 ml) required for complete combustion of S-benzylthiuronium chloride was 2.67.

EXAMPLE 6

Except that 7.712 mg of S-benzylthiuronium chloride were used, sample was pretreated similarly to Example 1 to implement the IC measurement. As a result, to the theoretical contents (% by weight) of 17.49% for Cl and 15.82% for S in S-benzylthiuronium chloride, 17.31% and 15.70% were obtained for Cl and S, respectively.

Besides, in this example, the ratio of the amount of oxygen (=40.2 ml) at heating section to the theoretical amount of oxygen (=12.6 ml) required for complete combustion of S-benzylthiuronium chloride was 3.19.

EXAMPLE 7

Except that 2.282 mg of S-benzylthiuronium chloride were inserted into the closed heat-decomposing appliance used in Example 4 and the closed heat-decomposing appliance was inserted as far as 15 cm into circular electric furnace from the side of sample, sample was pretreated similarly to Example 1 to implement the IC measurement. As a result, to the theoretical contents (by weight) of 17.49% for Cl and 15.82% for S in S-benzylthiuronium chloride, 17.31% and 15.54% were obtained for Cl and S, respectively.

Besides, in this example, the ratio of the amount of oxygen (=11.8 ml) at heating section to the theoretical amount of oxygen (=3.72 ml) required for complete combustion of S-benzylthiuronium chloride was 3.17.

EXAMPLE 8

Except that S-benzylthiuronium chloride was placed in a quartz boat (length: 5 mm, width: 15 mm, height: 3 mm), sample was pretreated similarly Example 1 to implement the IC measurement. As a result, to the theoretical contents (% by weight) of 17.49% for Cl and 15.82% for S in S-benzylthiuronium chloride, 17.42% and 15.74% was obtained for Cl and S, respectively.

EXAMPLE 9

Except that S-benzylthiuronium chloride was placed in a alumina ceramic boat (length: 5 mm, width: 15 mm, height: 4 mm), sample was pretreated similarly Example 1 to implement the IC measurement. As a result, to the theoretical contents (% by weight) of 17.49% for Cl and 15.82% for S in S-benzylthiuronium chloride, 17.31% and 15.66% was obtained for Cl and S, respectively.

EXAMPLE 10

Except that S-benzylthiuronium chloride was accommodated in a sampling vessel and weighed accurately, and, after dropped sample alone in the closed heat-decomposing appliance, the sampling vessel was weighed accurately to determine the quantity of sample, sample was treated similarly to Example 4 to implement the IC measurement similarly to Example 1. As a result, to the theoretical contents (% by weight) of 17.49% for Cl and 15.82% for S in S-benzylthiuronium chloride, 17.66% and 15.79% were obtained for Cl and S, respectively.

EXAMPLE 11

Except that the shape of the closed heat-decomposing appliance used in Example 1 was made to be length of tube of 18 cm, inner diameter of tube of 27 mm and outer diameter of tube of 30 mm, S-benzylthiuronium chloride was inserted thereinto and the closed heat-decomposing appliance was inserted as far as 10 cm into circular electric furnace from the side of sample, sample was pretreated similarly to Example 8 to implement the IC measurement similarly to Example 1. As a result, to the theoretical contents (% by weight) of 17.49% for Cl and 15.82% for S in S-benzylthiuronium chloride, 17.45% and 15.55% were obtained for Cl and S, respectively.

EXAMPLE 12

Except that S-benzylthiuronium chloride was inserted into the closed heat-decomposing appliance (length of tube: 30 cm, inner diameter of tube: 16 mm, outer diameter of tube: 18 mm) shown in FIG. 2, sample was pretreated similarly Example 1 to implement the IC measurement. As a result, to the theoretical contents (% by weight) of 17.49% for Cl and 15.82% for S in S-benzylthiuronium chloride, 17.56% and 15.65% were obtained for Cl and S, respectively.

EXAMPLE 13

Except that S-benzylthiuronium chloride was inserted into the closed heat-decomposing appliance (length of tube: 30 cm, inner diameter of tube: 16 mm, outer diameter of tube: 18 mm) shown in FIG. 3, sample was pretreated similarly Example 1 to implement the IC measurement. As a result, to the theoretical contents (% by weight) of 17.49% for Cl and 15.82% for S in S-benzylthiuronium chloride, 17.32% and 15.66% were obtained for Cl and S, respectively.

EXAMPLE 14

Except that S-benzylthiuronium chloride was inserted into the closed heat-decomposing appliance (length of tube: 30 cm, inner diameter of tube: 16 mm, outer diameter of tube: 18 mm) shown in FIG. 4, sample was pretreated similarly Example 1 to implement the IC measurement. As a result, to the theoretical contents (% by weight) of 17.49% for Cl and 15.82% for S in S-benzylthiuronium chloride, 17.57% and 15.79% were obtained for Cl and S, respectively.

EXAMPLE 15

Except that the closed heat-decomposing appliance was inserted by slanting 30° to horizontal, making the closed introducing section down, sample was pretreated similarly Example 1 to implement the IC measurement. As a result, to the theoretical contents (% by weight) of 17.49% for Cl and 15.82% for S in S-benzylthiuronium chloride, 17.28% and 15.82% were obtained for Cl and S, respectively.

EXAMPLE 16

Except that an aqueous solution of 0.04 mol/L sodium hydroxide and 10% by weight of hydrazine were used for the absorbing liquid, sample was pretreated similarly Example 2 to implement the IC measurement similarly to Example 1. As a result, to the content (% by weight) of 9.73% for Br in this substance, 9.55% was obtained for Br.

EXAMPLE 17

Except that p-chlorobenzoic acid was used for the sample and pure water was used for the absorbing liquid, sample was pretreated similarly Example 4 to implement the IC measurement similarly to Example 1. As a result, to the theoretical content (% by weight) of 22.64% for Cl in this substance, 22.00% was obtained for Cl.

EXAMPLE 18

Except that the same closed heat-decomposing appliance as that in Example 4, excluding use of hard glass as a material, and sample boat were used, and the temperature of furnace and heating time were made to be 600° C. and 30 minutes, respectively, sample was treated similarly to Example 4 to implement the IC measurement similarly to Example 1. As a result, the theoretical contents (% by weight) of 17.49% for Cl and 15.82% for S in S-benzylthiuronium chloride, 17.90 % and 15.43% were obtained for Cl and S, respectively.

EXAMPLE 19

Except that the same closed-heat decomposing appliance as that in Example 1, excluding use of alumina ceramic as a material, was used, sample was pretreated similarly to Example 1 to implement the IC measurement. As a result, to the theoretical contents (% by weight) of 17.49% for Cl and 15.82% for S in S-benzylthiuronium chloride, 17.44% and 15.77% were obtained for Cl and S, respectively.

EXAMPLE 20

Except that o-iodobenzoic acid was used for the sample and absorbing liquid comprising an aqueous solution of 0.04 mol/L sodium hydroxide, 24% by weight of hydrogen peroxide and 10% by weight of hydrazine was used, sample was pretreated similarly to Example 1 to implement the IC measurement. As a result, to the theoretical content (% by weight) of 15.17% for I in this substance, 15.09% was obtained for I.

From the examples as above, it was seen that, by pretreating the organic compounds containing various halogens and sulfur using the inventive appliance and measuring the contents of halogen and sulfur in the pretreatment liquids obtained, they are determined accurately as shown by low RSD, and further almost 100% recovery rates lead to accurate measurement results.

As having described above, according to the invention, following advantages can be achieved,
1) There is little contamination due to no combustion assistant used.
2) There are no complicated dangerous procedures, comparing with conventional methods implementing firing of sample and combustion in flask, sealing tube operation, insertion of sample into heating area and rotation of heat-decomposing tube together with furnace.
3) Since the absorbing liquid is injected after heating, there are no anxieties of increased inner pressure due to evaporation on heating and evaporation of absorbing liquid.
4) There is no obstruction due to ash present in the sample, thereby the testing components can be quantitatively analyzed accurately.
5) The inventive appliance can be used repeatedly.

In addition, the pretreatment device and analytical device using the inventive appliance are useful industrially, since their procedures can be automated while making the best use of such advantages.

What is claimed is:

1. A method for heat-decomposing a sample containing organics using a heat-decomposing device comprising a heat-decomposing appliance, said method comprising the steps of
   setting up the sample in the heat-decomposing appliance comprising, in the absence of firing means:
   a) a heating section in the form of an axially aligned tube, open at only one of two opposing axial ends, having a length between said opposing axial ends of at least 10 cm and being molded of material that withstands (i) corrosive gases, (ii) oxidative corrosion, and (iii) heating to a temperature of at least 600° C.; and
   b) an introducing section that cooperates with the open end of said tube to seal the open end and, thereby, close said heating tube for heat decomposition when containing organic components, said introducing section including means for introducing liquid through said introducing section into said heating tube when closed;
   heating of said appliance being effected only by external means, said appliance containing no source of heat;
   filling up the appliance with oxygen and closing the appliance, then heating the appliance to decompose the organics into testing components, followed by cooling the appliance, and thereafter introducing an absorbing liquid into said heat-decomposing appliance to absorb the testing components produced in said sample,
   said heat-decomposing device further comprising an appliance-installing section to install said closed heat-decomposing appliance, a heating means to heat-decompose the sample in said closed heat-decomposing appliance and a moving means to reversibly move said closed heat-decomposing appliance installed at said appliance-installing section to said heating means.

2. The method of claim 1 for heat-decomposing a sample and dissolving testing components produced, said device further comprising cooling means to cool the heat-decomposing appliance after heat-decomposition of the sample in said heat-decomposing appliance, injecting means to inject the absorbing liquid into said cooled heat-decomposing appliance, mixing means to stir and/or shake for making the absorbed liquid in said heat-decomposing appliance uniform, and moving means to reversibly move said heat-decomposing appliance from an appliance-installing section to any of said heating means, cooling means, injecting means or mixing means.

3. The method of claim 2, further comprising stirring and/or shaking said heat-decomposing appliance to make said absorbed liquid in the heat-decomposing appliance uniform.

4. The method of claim 2 further comprising analyzing the testing components, the device further comprising analytical means to analyze the testing components in the absorbing liquid and sampling means to sample the absorbed liquid inside the heat-decomposing appliance and move the absorbed-liquid sample to said analytical means.

5. The method of claim 4, said heat-decomposing device further comprising a wash device containing:
   c) a needle pipe for injecting absorbing liquid into the heat-decomposing appliance,
   d) a motor buret,
   e) a switchable valve with actuator, f) a washing port to wash the needle pipe, and g) means for moving the needle pipe to pierce through packing or septum of the introducing section of the heat-decomposing appliance and, then, move the needle pipe to the washing port.

6. The method of claim 4, said mixing means comprising means to reciprocate the heat-decomposing appliance in the axial direction while axially rotating the heat-decomposing appliance horizontally.

7. The method of claim 4, said moving means comprising a cross type motor robot with a mechanical hand or a mechanical hand and cross type motor robot with axis for rotating it.

8. A device for heat-decomposing a sample containing organics comprising:

a heat-decomposing appliance comprising, in the absence of firing means:

a) a heating section in the form of an axially aligned tube, open at only one of two opposing axial ends, having a length between said opposing axial ends of at least 10 cm and being molded of material that withstands (i) corrosive gases, (ii) oxidative corrosion, and (iii) heating to a temperature of at least 600° C.; and b) an introducing section that cooperates with the open end of said tube to seal the open end and, thereby, close said heating tube for heat decomposition when containing organic components, said introducing section including means for introducing liquid through said introducing section into said heating tube when closed; heating of said appliance being effected only by external means, said appliance containing no source of heat;

an appliance-installing section to install said closed heat-decomposing appliance, a heating means to heat-decompose the sample in said closed heat-decomposing appliance, and a moving means to reversibly move said closed heat-decomposing appliance installed at said appliance-installing section to said heating means.

9. The device of claim 8 further comprising cooling means to cool the heat-decomposing appliance after heat-decomposition of the sample in said heat-decomposing appliance, injecting means to inject the absorbing liquid into said cooled heat-decomposing appliance, mixing means to stir and/or shake for making the absorbed liquid in said heat-decomposing appliance uniform, and moving means to reversibly move said heat-decomposing appliance from an appliance-installing section to any of said heating means, cooling means, injecting means, or mixing means.

10. The device of claim 9 further comprising analytical means to analyze the testing components in the absorbing liquid and sampling means to sample the absorbed liquid inside the heat-decomposing appliance and move the absorbed-liquid sample to said analytical means.

11. The device of claim 10, further comprising a wash device containing:

a) a needle pipe for injecting absorbing liquid into the heat-decomposing appliance, b) a motor buret, c) a switchable valve with actuator, d) a washing port to wash the needle pipe, and e) means for moving the needle pipe to pierce through packing or septum of the introducing section of the heat-decomposing appliance and, then, move the needle pipe to the washing port.

12. The device of claim 10, said mixing means comprising means to reciprocate the heat-decomposing appliance in the axial direction while axially rotating the heat-decomposing appliance horizontally.

13. The device of claim 10, said moving means comprising a cross type motor robot with a mechanical hand or a mechanical hand and cross type motor robot with axis for rotating it.

* * * * *

UNITED STATES PATENT AND TRADEMARK OFFICE
CERTIFICATE OF CORRECTION

PATENT NO. : 6,960,477 B2
APPLICATION NO. : 09/774641
DATED : November 1, 2005
INVENTOR(S) : Tanimoto et al.

It is certified that error appears in the above-identified patent and that said Letters Patent is hereby corrected as shown below:

Column 4, line 28, change "organic s" to --organics--

Column 10, line 2, change "In FIG. 2, numeral" to --In FIG. 3, numeral--

Column 11, line 41, change "kx" to --by--

Column 13, line 7, change "liquid into the" to --liquid to the--

Column 14, line 13, change "and infected into" to --and injected into--

Columns 15 and 16, in TABLE 1, the numerical data at the right end of Example 11 (the column of Amt. of oxygen at heating section/theoretical amt. of oxygen), change "8.61" to --6.61--

Column 18, line 8, change "glycerol glycerine" to --glycerine--

Signed and Sealed this

Twelfth Day of September, 2006

JON W. DUDAS
*Director of the United States Patent and Trademark Office*